United States Patent [19]

Acquista

[11] Patent Number: 4,683,874
[45] Date of Patent: Aug. 4, 1987

[54] BRONCHOFIBERSCOPE

[76] Inventor: Angelo Acquista, 31-65 Cresent St., Astoria, N.Y. 11106

[21] Appl. No.: 827,065

[22] Filed: Feb. 7, 1986

[51] Int. Cl.⁴ .............................................. A61B 1/00
[52] U.S. Cl. ........................................... 128/6; 128/4
[58] Field of Search .......................... 128/4, 6, 10, 11; 604/265

[56] References Cited

U.S. PATENT DOCUMENTS 3,736,939  6/1973  Taylor .................................. 604/265

OTHER PUBLICATIONS

"A Fiberoptic Bronchoscopy Technique, etc." by Neil Wimberly et al., *American Review of Respiratory Disease,* vol. 119, pp. 337-343, 1979.

Microvasive Contamination-free Microbiology Specimen Brush, brochure, 2 pages, 12-1985.

*Primary Examiner*—William H. Grieb
*Attorney, Agent, or Firm*—Michael I. Kroll

[57] ABSTRACT

An improved bronchofiberscope is provided that contains a sterile and uncontaminated distal end of an insertion tube with sleeves and a disolvable membrane over it to facilitate the distal end past vocal cords so that the sleeves can be pulled back releasing the disolvable membrane to expose the distal end whereby viewing of a windpipe and the branches is done with a light guide and an objective lens and removal of bronchial secretions is facilitated through a suction/forceps channel to remove an uncontaminated specimen for an appropriate bacteriologic examination.

5 Claims, 4 Drawing Figures

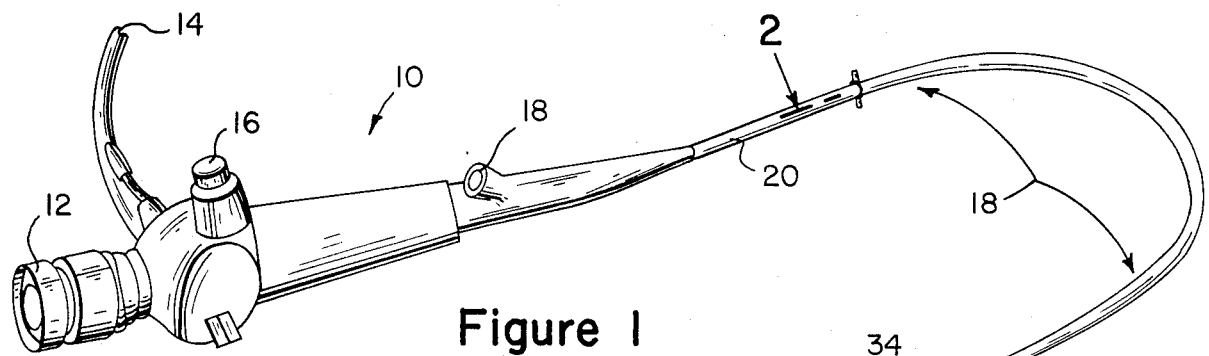
Figure 1
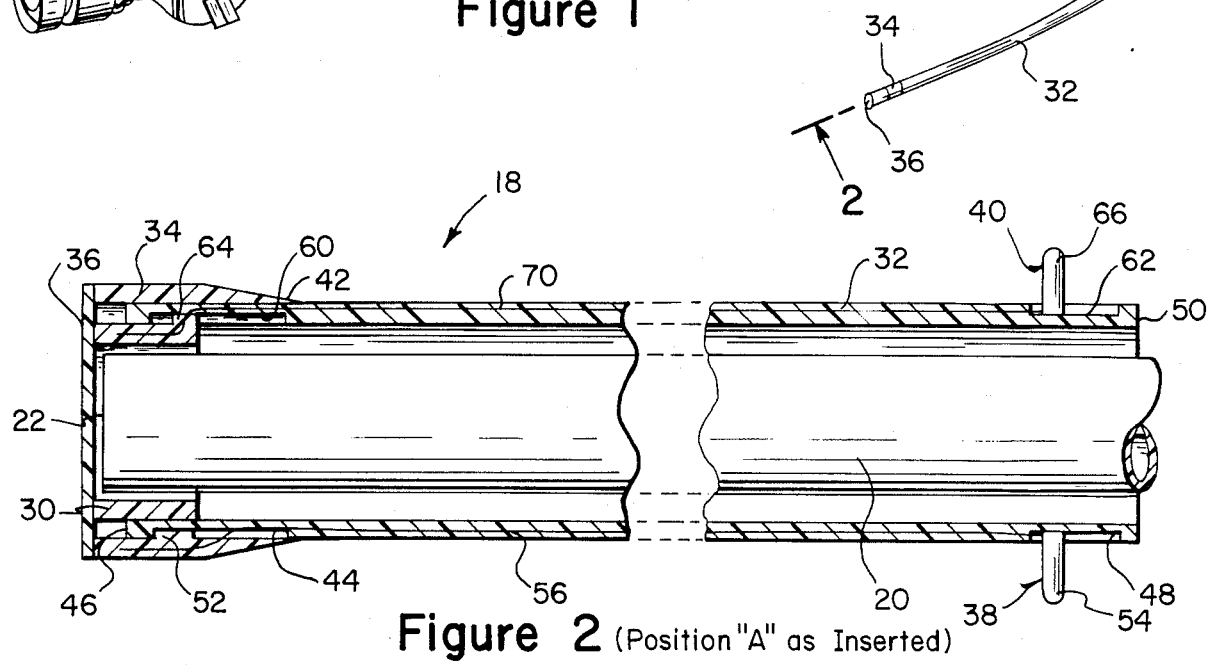
Figure 2 (Position "A" as Inserted)
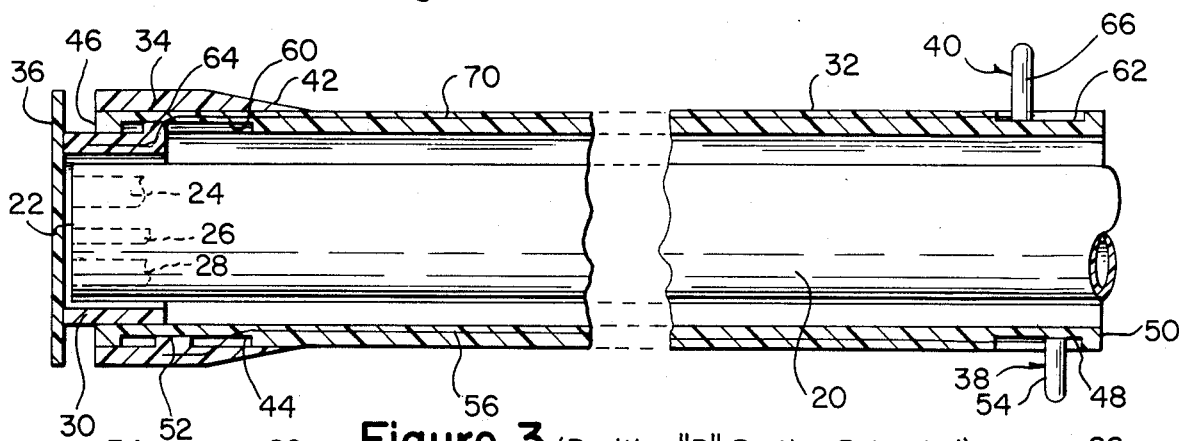
Figure 3 (Position "B" Partley Retracted)
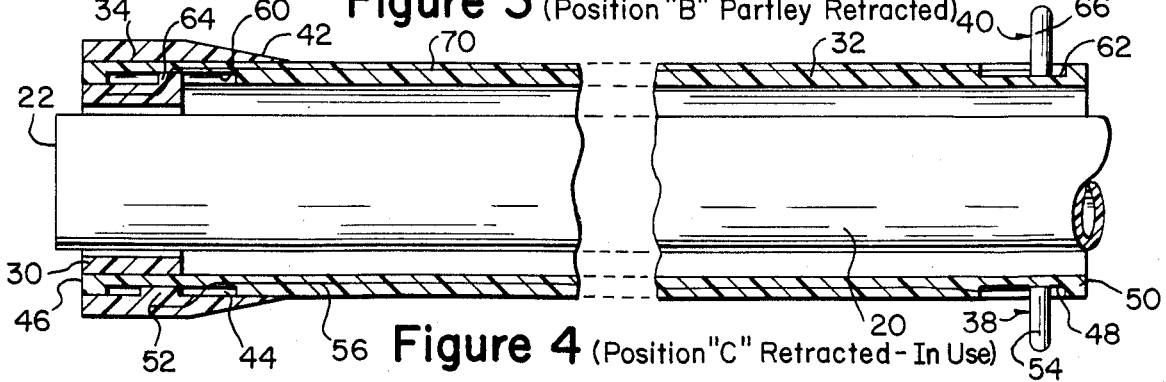
Figure 4 (Position "C" Retracted-In Use)

BRONCHOFIBERSCOPE

BACKGROUND OF THE INVENTION

1. Field of the Invention

The instant invention relates generally to endoscopes and more specifically it relates to an improved bronchofiberscope.

2. Description of the Prior Art

If a doctor wishes to look beyond the mouth, the rectum, or the urethra to see such areas as the stomach, the bladder, the esophagus, or the larynx, he must use a tube device that can be inserted into the patient's body. This tube is called the endoscope. Endo is the Greek word for "inside," which, combined with the Greek skopos, means "watcher of the inside." The endoscope is equipped with tiny electric lights and is passed into whichever body opening leads to the area to be studied. It comes in several types, each intended for certain areas of the body and each having a appropriate length and diameter. Both ends have specific names. The tip that enters the patient is called the distal end. The opposite tip is the proximal—or eyepiece—end.

The various kinds of endoscopes in use today are generally named according to their purpose. The tracheo-bronchoscope from Greek tracheo - windpipe, usually called simply the bronchoscope, examines the windpipe and its branches.

In addition to allowing the doctor to look inside the body, endoscopes can assist in certain kinds of surgery. For example, a surgeon may insert a long biting-type instrument into the bronchoscope to biopsy a growth in the windpipe—that is, to bring away a bit of tissue so that it may be microscopically examined to see if the growth is harmless or dangerous and needs to be removed.

Even more valuable and dramatic has been the development of the fiberscope. Prior to its day, the physician could not see around bends in the body's organs, and so it was impossible to examine some internal areas. The fiberscope marked an end to this shortcoming. It is a flexible tube made of fiber glass. The fiber glass takes the form of millions of tiny, parallel rods, all pointing to the end of the scope in such a way that they act as an unending chain or mirrors able to reflect light and the image of an organ right around corners. The trimuph of fiberoptic technology has provided the physician with the most complete means possible for endoscopic examination.

The oral and nasopharynx are colonized by numerous bacteria. Beyond the vocal cords, the trachea is sterile free of bacterial colonization. The nature of bronchoscopy requires passage of a flexible fiberoptic scope that is about 0.5 cm in diameter through the oral and or nasopharynx. It is through this passage that the distal end of the bronchoscope becomes contaminated by non-pathogenic colonizing bacteria. Consequently, fluid aspirated from the tracheobronchial tree is neither sensitive nor specific for the detection of pulmonary bacterial pathogens in pheumonic processes.

SUMMARY OF THE INVENTION

A primary object of the present invention is to provide an improved bronchofiberscope that will overcome the shortcomings of the prior art devices.

Another object is to provide a improved bronchofiberscope that contains sleeves which are sterile, form-fitting, elastic, polymer of a plastic which will add very little to the diameter of the distal end thereof.

An additional object is to provide an improved bronchofiberscope in which the sterile uncontaminated distal end with the sleeves over it are facilitated past the vocal cords so that the sleeves can be pulled back exposing the distal end. This distal end is then maneuvered into a subseqmental bronchus whereby the removal of bronchial secretions is facilitated by aspirating through a suction channel to remove a sterile specimen for the appropriate bacteriologic examination.

A further object is to provide an improved bronchofiberscope that is simple and easy to use.

A still further object is to provide an improved bronchofiberscope with disposable sterile sleeves that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of the invention positioned on a standard bronchoscope.

FIG. 2 is an enlarged cross sectional view with parts broken away taken along line 2—2 in FIG. 1 showing the distal end as inserted.

FIG. 3 is an enlarged cross sectional view with parts broken away similar to FIG. 2 showing the sleeves partly retracted.

FIG. 4 is an enlarged cross sectional view with parts broken away similar to FIG. 3 showing the sleeves completely retracted with the distal end in use.

DETAILED DESCRIPTION OF THE PREFERRED EMBODIMENTS

Turning now descriptively to the drawings, in which similar reference characters denote similar elements throughout the several views, FIGS. 1 through 4 illustrate an improved bronchofiberscope 10 of the type that has a proximal eyepiece end 12 with light source 14, suction button 16 and channel inlet 18 and an insertion tube 20 with a distal end 22 that includes an objective lens 24, light guide 26 and suction/forceps channel 28.

The improvement consists of a short inner sleeve 30, an elongated outer sleeve 32, a head sleeve 34, a disolvable membrane 36, a first retracting device 38 and a second retracting device 40.

The short inner sleeve 30 retractably fits over the distal end 22 of the insertion tube 20. The elongated outer sleeve 32 fits over the insertion tube 20 to just before the distal end 22 thereof. The head sleeve 34 retractably fits over the elongated outer sleeve 32 and the short inner sleeve 30 over the distal end 22 of the insertion tube 20. The disolvable membrane 36 covers the distal end 22 of the insertion tube 20, the short inner sleeve 30 and the head sleeve 34 to keep the distal end sterile and uncontaminated (see postion "A" in FIG. 2).

The first retracting device 38 is for retracting the head sleeve 34 back over the elongated outer sleeve 32 to release the head sleeve from the disolvable membrane 36. The second retracting device 40 is for retracting the short inner sleeve 30 back over the distal end 22 of the insertion tube 20 to release the short inner sleeve from the disolvable membrane 36 to expose the sterile and uncontaminated distal end 22. Viewing of a windpipe and its branches is done with the light guide 26 and the objective lens 24. Sterile removal of bronchial secretions is faciliated through the suction/forceps channel 28 to remove uncontaminated specimen for an appropriate bacteriologic examination.

The short inner sleeve 30, the elongated outer sleeve 32 and the head sleeve 34 are fabricated out of sterile, inert, form-fitting, elastic, polymer plastic which will add very little to the diameter of the distal end 22 of the insertion tube 20. The head sleeve 34 is tapered rearwardly at 42 to facilitate retractions.

The first retracting device 38 includes the elongated outer sleeve 32 having a first external groove 44 formed at forward end 46 and a second external groove 48 formed at rearward end 50. The head sleeve 34 has an internal tongue 52 to slide within the first external groove 44 of the elongated outer sleeve 32. A first retraction lever 54 slides within the second external groove 48 of the elongated outer sleeve 32. A first retraction wire 56 extends generally through the elongated outer sleeve 32 between the head sleeve 34 and the first retraction lever 54. When the first retraction lever 54 is pulled backwards, the head sleeve 34 will go back over the elongated outer sleeve 32. (See position "B" in FIG. 3).

The second retracting device 40 includes the elongated outer sleeve 32 having an internal groove 60 formed at the forward end 46 and a third external groove 62 formed at the rearward end 50. The short inner sleeve 30 has an external tongue 64 to slide within the internal groove 60 of the elongated outer sleeve 32. A second retraction lever 66 slides within the third external groove 62 of the elongated outer sleeve 32. A second retraction wire 70 extends generally through the elongated outer sleeve 32 between the short inner sleeve 30 and the second retraction lever 66. When the second retraction lever 66 is pulled backwards the short inner sleeve 30 will go back over the distal end 22 of the insertion tube 32 (see position "C" in FIG. 4).

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An improved bronchofiberscope of the type having a proximal eyepiece end with light source, suction button and channel inlet and an insertion tube with a distal end including an objective lens, light guide and suction/forceps channel, wherein the improvement comprises:
    (a) a short inner sleeve that retractably fits over said distal end of said insertion tube;
    (b) an elongated outer sleeve that fits over said insertion tube to just before said distal end thereof;
    (c) a head sleeve that retractably fits over said elongated outer sleeve and said short inner sleeve over said distal end of said insertion tube;
    (d) a disolvable membrane that covers said distal end of said insertion tube, said short inner sleeve and said head sleeve to keep said distal end sterile and uncontaminated;
    (e) a first means for retracting said head sleeve back over said elongated outer sleeve to release said head sleeve from said disolvable membrane; and
    (f) a second means for retracting said short inner sleeve back over said distal end of said insertion tube to release said short inner sleeve from said disolvable membrane to expose said sterile and uncontaminated distal end whereby viewing of windpipe and its branches is done with said light guide and said objective lens and sterile removal of bronchial secretions is facilitated through said suction/forceps channel to remove an uncontaminated specimen for an appropriate bacteriologic examination.

2. An improved bronchofiberscope as recited in claim 1, wherein said short inner sleeve, said elongated outer sleeve and said head sleeve are fabricated out of sterile, form-fitting, elastic inert polymer plastic which will add very little to diameter of said distal end of said insertion tube.

3. An improved bronchofiberscope as recited in claim 2, wherein said head sleeve is tapered rearwardly to facilitate retraction.

4. An improved bronchofiberscope as recited in claim 3, wherein said first retracting means includes:
    (a) said elongated outer sleeve having a first external groove formed at forward end and a second external groove formed at rearward end;
    (b) said head sleeve having an internal tongue to slide within said first external groove of said elongated outer sleeve;
    (c) a first retraction lever to slide within said second external groove of said elongated outer sleeve; and
    (d) a first retraction wire extending generally through said elongated outer sleeve between said head sleeve and said first retraction lever so that when said first retraction lever is pulled backwards said head sleeve will go back over said elongated outer sleeve.

5. An improved bronchofiberscope as recited in claim 4, wherein said second retracting means includes:
    (a) said elongated outer sleeve having an internal groove formed at said forward end and a third external groove formed at said rearward end;
    (b) said short inner sleeve having an external tongue to slide within said internal groove of said elongated outer sleeve;
    (c) a second retraction lever to slide within said third external groove of said elongated outer sleeve; and
    (d) a second retraction wire extending generally through said elongated outer sleeve between said short inner sleeve and said second retraction lever so that when said second retraction lever is pulled backwards said short inner sleeve will go back over said distal end of said insertion tube.

* * * * *